United States Patent
MacQueen et al.

(10) Patent No.: US 10,882,804 B2
(45) Date of Patent: Jan. 5, 2021

(54) METHODS AND COMPOSITIONS FOR HYDRODEOXYGENATION OF CARBOHYDRATES AND CARBOHYDRATE ANALOGS

(71) Applicant: UNIVERSITY OF SOUTH CAROLINA, Columbia, SC (US)

(72) Inventors: Blake H. MacQueen, Columbia, SC (US); Elizabeth Barrow, Ladson, SC (US); Jochen Lauterbach, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 16/547,974

(22) Filed: Aug. 22, 2019

(65) Prior Publication Data

US 2020/0087234 A1    Mar. 19, 2020

Related U.S. Application Data

(60) Provisional application No. 62/790,509, filed on Jan. 10, 2019, provisional application No. 62/731,164, filed on Sep. 14, 2018.

(51) Int. Cl.
*C07C 29/141* (2006.01)
*C07C 31/22* (2006.01)
(Continued)

(52) U.S. Cl.
CPC ......... *C07C 29/141* (2013.01); *B01J 23/6567* (2013.01); *C07C 29/132* (2013.01);
(Continued)

(58) Field of Classification Search
CPC ... C07C 29/132; C07C 29/141; C07C 29/145; C07C 29/48; C07C 31/22; C07C 31/24;
(Continued)

(56) References Cited

U.S. PATENT DOCUMENTS 2,097,493 A * 11/1937 Pokorny ................. C07C 31/18
568/865
3,586,537 A    6/1971 Steiner et al.
(Continued)

FOREIGN PATENT DOCUMENTS

CN    103131802    6/2013

OTHER PUBLICATIONS

Deng T.Y., et al., Cellulose conversin to polyols on supported Ru catalysts in aqueous basic solution, 2010, Science China, Chemistry, vol. 53, No. 7, pp. 1476-1480 (Year: 2010).*
(Continued)

*Primary Examiner* — Yate' K Cutliff
(74) *Attorney, Agent, or Firm* — Dority & Manning. P.A.

(57) ABSTRACT

This disclosure provides embodiments directed to compositions, methods, and processes to produce compounds having the structure:

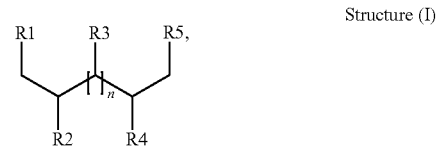

Structure (I)

each of R1-R5 is selected from a hydroxyl group and hydrogen; and R1-R5 include at least one hydroxyl group and at least one hydrogen; and n=0-2. In particular, methods of the disclosure can include reacting a precursor, the precursor containing more oxygen (O) atoms than the compound, with a gas containing hydrogen ($H_2$) in the presence of a catalyst.

18 Claims, 8 Drawing Sheets

(51) Int. Cl.
  *B01J 23/656* (2006.01)
  *C08L 97/02* (2006.01)
  *C07C 29/145* (2006.01)
  *C07C 29/132* (2006.01)

(52) U.S. Cl.
  CPC ............ *C07C 29/145* (2013.01); *C07C 31/22* (2013.01); *C08L 97/02* (2013.01); *B01J 2523/3712* (2013.01); *B01J 2523/74* (2013.01); *B01J 2523/824* (2013.01)

(58) Field of Classification Search
  CPC ... C07C 31/18; B01J 23/6567; B01J 2523/74; B01J 2523/824; B01J 2523/3712
  See application file for complete search history.

(56) References Cited

U.S. PATENT DOCUMENTS

| | | | |
|---|---|---|---|
| 3,784,408 A | 1/1974 | Jaffe et al. | |
| 5,424,417 A | 6/1995 | Torget et al. | |
| 6,291,725 B1* | 9/2001 | Chopade | C07C 29/00 568/861 |
| 7,109,005 B2 | 9/2006 | Eroma et al. | |
| 8,846,984 B2* | 9/2014 | Allgeier | B01J 27/188 549/427 |
| 9,018,423 B2* | 4/2015 | Allgeier | C07C 29/60 568/861 |
| 9,206,098 B2* | 12/2015 | Schuth | C07C 31/26 |
| 2003/0186805 A1* | 10/2003 | Vanderspurt et al. | C01F 17/00 502/304 |

OTHER PUBLICATIONS

Ota, et al., Hydrogenation of vicinal OH groups over heterogeneous Rhenium catalyst promoted by Palladium and Ceria support, 2015, Angew. Chem. Int. Ed., 54(6), pp. 1897-1900 (Year: 2015).*
Alonso, et al. "Bimetallic Catalysts for Upgrading of Biomass to Fuels and Chemicals" *Chem. Soc. Rev.* 41(24) (2012) pp. 8075-8098.
Amada, et al. "Selective Hydrodeoxygenation of Cyclic Vicinal Diols to Cyclic Alcohols over Tungsten Oxide-Palladium Catalysts" *ChemSusChem* 7(8) (2014) pp. 2185-2192.
Ballantyne, et al. "Reduce Optimisation Time and Effort: Taguchi Experimental Design Methods" *Forensic Sci. Int. Genet. Suppl. Ser.* 1(1) (2008) pp. 7-8.
Bruehwiler, et al. "Three-Phase Catalytic Hydrogenation of a Functionalized Alkyne: Mass Transfer and Kinetic Studies with in Situ Hydrogen Monitoring" *Ind. Eng. Chem. Res.* 47(18) (2008) pp. 6862-6869.
Bu, et al. "A Review of Catalytic Hydrodeoxygenation of Lignin-Derived Phenols from Biomass Pyrolysis" *Bioresour. Technol.* 124 (2012) pp. 470-477.
Cao, et al. "Direct Synthesis of Unsaturated Sugars from Methyl Glycosides" *ACS Catal.* 9 (2019) pp. 3725-3729.
Centeno, et al. "Influence of the Support of CoMo Sulfide Catalysts and of the Addition of Potassium and Platinum on the Catalytic Performances for the Hydrodeoxygenation of Carbonyl, Carboxyl, and Guaiacol-Type Molecules" *J. Catal.* 154 (1995) pp. 288-298.
Crespo-Quesada, et al. "Kinetics of the Solvent-Free Hydrogenation of 2-Methyl-3-Butyn-2-Ol over a Structured Pd-Based Catalyst" *Catal. Today* 147(3-4) (2009) pp. 247-254.
Engel, et al. "Taguchi Parameter Design by Second-Order Response Surfaces" *Qual. Reliab. Eng. Int.* 12 (1996) pp. 95-100.
Grilc, et al. "Hydrodeoxygenation of Solvolysed Lignocellulosic Biomass by Unsupported $MoS_2$, $MoO_2$, $Mo_2C$ and $WS_2$ catalysts" *Appl. Catal., B* 163 (2015) pp. 467-477.
Gutierrez, et al. "Hydrodeoxygenation of Guaiacol on Noble Metal Catalysts" *Catal. Today* 147(3-4) (2009) pp. 239-246.
Jin, et al. "Catalytic Transfer Hydrogenation of Biomass-Derived Substrates to Value-Added Chemicals on Dual-Function Catalysts: Opportunities and Challenges" *ChemSusChem* 12 (2019) pp. 71-92.
Laskar, et al. "Noble-Metal Catalyzed Hydrodeoxygenation of Biomass-Derived Lignin to Aromatic Hydrocarbons" *Green Chem.* 16(2) (2014) pp. 897-910.
Lee, et al. "Catalytic Roles of Metals and Supports on Hydrodeoxygenation of Lignin Monomer Guaiacol" *Catal. Commun.* 17 (2012) pp. 54-58.
Luierbacher, et al. "Targeted Chemical Upgrading of Lignocellulosic Biomass to Platform Molecules" *Green Chem.* 16(12) (2014) pp. 4816-4838.
Melin, et al. "Evaluation of Lignocellulosic Biomass Upgrading Routes to Fuels and Chemicals" *Cellul. Chem. Technol.* 44(4-6) (2010) pp. 117-137.
Nakagawa, et al. "Catalytic Total Hydrodeoxygenation of Biomass-Derived Polyfunctionalized Substrates to Alkanes" *ChemSusChem* 8(7) (2015) pp. 1114-1132.
Ota, et al. "Performance, Structure, and Mechanism of $ReO_x$—Pd/$CeO_2$ Catalyst for Simultaneous Removal of Vicinal OH Groups with $H_2$" *ACS Catal.* 6(5) (2016) pp. 3213-3226.
Ota, et al. "Hydrodeoxygenation of Vicinal OH Groups over Heterogeneous Rhenium Catalyst Promoted by Palladium and Ceria Support" *Angew. Chem., Int. Ed.* 54(6) (2015) pp. 1897-1900.
Parks, J.M. "On Stochastic Optimization. Taguchi Methods™ Demystified; Its Limitations and Fallacy Clarified" *Prob. Eng. Mech.* 16 (2001) pp. 87-101.
Prasomsri, et al. "Effective Hydrodeoxygenation of Biomass-Derived Oxygenates into Unsaturated Hydrocarbons by $MoO_3$ Using Low $H_2$ Pressures" *Energy Environ. Sci.* 6(6) (2013) pp. 1732-1738.
Rao, et al. "Bioconversion of Lignocellulosic Biomass to Xylitol: An Overview" *Bioresour. Technol.* 213 (2016) pp. 299-310.
Ren, et al. "Selective Hydrodeoxygenation of Biomass-Derived Oxygenates to Unsaturated Hydrocarbons Using Molybdenum Carbide Catalysts" *ChemSusChem* 6(5) (2013) pp. 798-801.
Saha, et al. "Zinc-Assisted Hydrodeoxygenation of Biomass-Derived 5-Hydroxymethylfurfural to 2,5-Dimethylfuran" *ChemSusChem* 7(11) (2014) pp. 3095-3101.
Sandbrink, et al. "Supported Molybdenum Catalysts for the Deoxydehydration of 1,4-Anhydroerythritol into 2,5-Dihydrofuran" *ChemSusChem* 10(7) (2017) pp. 1375-1379.
Senol, et al. "Hydrodeoxygenation of Methyl Esters on Sulphided NiMo/γ—$Al_2O_3$ and CoMo/γ—$Al_2O_3$ Catalysts" *Catal. Today* 100(3-4) (2005) pp. 331-335.
Shakeri, et al. "A Comparative Study of the Counterion Effect on the Perrhenate-Catalyzed Deoxydehydration Reaction" *Mol. Catal.* 471 (2019) pp. 27-37. (Abstract only).
Stalpaert, et al. "Stabilizing Effect of Bulky β-Diketones on Homogeneous Mo Catalysts for Deoxydehydration" *ACS Sust. Chem. Eng.* 6 (2018) pp. 12197-12204.
Tamura, et al. "Heterogeneous Catalysis Transformation of Sugars into Chiral Polyols over a Heterogeneous Catalyst" *Angew. Chem.* 57 (2018) pp. 8058-8062.
Tazawa, et al. "Deoxydehydration with Molecular Hydrogen over Ceria-Supported Rhenium Catalyst with Gold Promoter" *ACS Catal.* 6(10) (2016) pp. 6393-6397.
Vernuccio, et al. "General Kinetic Modeling of the Selective Hydrogenation of 2-Methyl-3-Butyn-2-Ol over a Commercial Palladium-Based Catalyst" *Ind. Eng. Chem. Res.* 54(46) (2015) pp. 11543-11551.
Wang, et al. "Influence of Acid Pretreatment on the Hydrodeoxygenation Performance of Carbon Supported RuMo Bimetallic Catalysts on Sorbitol Conversion" *SN Appl. Sci.* 1(404) (2019) pp. 1-10.
Wang, et al. "One-Pot Catalytic Selective Synthesis of 1,4-butanediol from 1,4-anhydroerythritol and hydrogen" *Green Chem.* 20 (2018) pp. 2547-2557.
Xi, et al. "Mechanistic Study of the Ceria Supported, Re-Catalyzed Deoxydehydration of Vicinal Oh Groups" *Catal. Sci. Technol.* 8(22) (2018) pp. 5750-5762.
Zhao, et al. "Aqueous-Phase Hydrodeoxygenation of Bio-Derived Phenols to Cycloalkanes" *J. Catal.* 280(1) (2011) pp. 8-16.

(56) References Cited

OTHER PUBLICATIONS

Zhao, et al. "Hydrodeoxygenation of Bio-Derived Phenols to Hydrocarbons Using Raney® Ni and Nafion/$SiO_2$ Catalysts" *Chem. Commun.* 46(3) (2010) pp. 412-414.

* cited by examiner

METHODS AND COMPOSITIONS FOR HYDRODEOXYGENATION OF CARBOHYDRATES AND CARBOHYDRATE ANALOGS

CROSS-REFERENCE TO RELATED APPLICATIONS

The present application claims the benefit of U.S. Provisional Patent Application Ser. No. 62/790,509, filed Jan. 10, 2019, and 62/731,164, filed Sep. 14, 2018. Each of the foregoing patent applications is hereby incorporated by reference in its entirety.

STATEMENT AS TO RIGHTS TO INVENTIONS MADE UNDER FEDERALLY SPONSORED RESEARCH

This invention was made with Government support under Contract Nos. 1632824 and 1250052, awarded by the National Science Foundation (NSF). The Government has certain rights in the invention.

BACKGROUND

Lignocellulosic biomass upgrading can provide an invaluable tool for producing value chemicals using widely-available, renewable resources. Lignocellulosic biomass refers to an organic material derived from plants, such as wood chips, pine straw, sawdust, and similar materials. After drying, each of these materials is mainly composed of a complex mixture of polysaccharides which can be fermented to produce ethanol as a basic fuel additive. However, other derivates from lignocellulosic biomass, such as carbohydrates (e.g., di- or monosaccharides) or carbohydrate analogs, may provide useful starting materials for synthesizing value chemicals without requiring fossil fuels.

Polysaccharides are carbohydrate polymers, and various reforming methods can be used to process polysaccharides to obtain the carbohydrate oligomers and monomers. Generally, carbohydrates refer to any compound having a chemical formula of the form $C_x(H_2O)_x$, where x determines the size. Common carbohydrate monomers include pentoses (x=5) and hexoses (x=6). Carbohydrate analogs can be produced by oxidative or reductive processes. For example, sugar alcohols are a reduced form of the starting sugar in which the carbonyl group been reduced to a hydroxyl, and sugar acids are an oxidized form of the starting sugar in which the carbonyl group has been oxidized to a carboxylic acid.

Generally, carbohydrates and carbohydrate analogs can be difficult to process due to the many functional groups. Some efforts have been put forth in processing carbohydrates to low carbon solvents e.g., methanol, ethanol, tetrahydrofuran, 2,5-dihydrofuran, and 3-Hydroxytetrahydrofuran. However, processes for generating larger, acyclic high value chemicals are lacking.

SUMMARY OF THE INVENTION

This disclosure provides embodiments directed to compositions, methods, and processes to produce compounds having the structure:

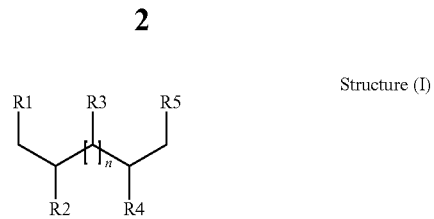

Structure (I)

each of R1-R5 is selected from a hydroxyl group and hydrogen; R1-R5 include at least one hydroxyl group and at least one hydrogen; n=0-2. In particular, methods of the disclosure can include reacting a precursor, the precursor containing more oxygen (O) atoms than the compound, with a gas containing hydrogen ($H_2$) in the presence of a catalyst.

For embodiments of the disclosure, generally the catalyst can be formed from a support impregnated with one or more transition metals. In an example embodiment, the precursor can be a carbohydrate or a carbohydrate derivative. In another example embodiment, the carbohydrate or carbohydrate derivate can be an aldose, a ketose, a sugar alcohol, or a sugar acid. In some embodiments, the precursor can be derived from lignocellulose-containing material or biomass that includes cellulose, hemicellulose, or lignin.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

Figure 1:
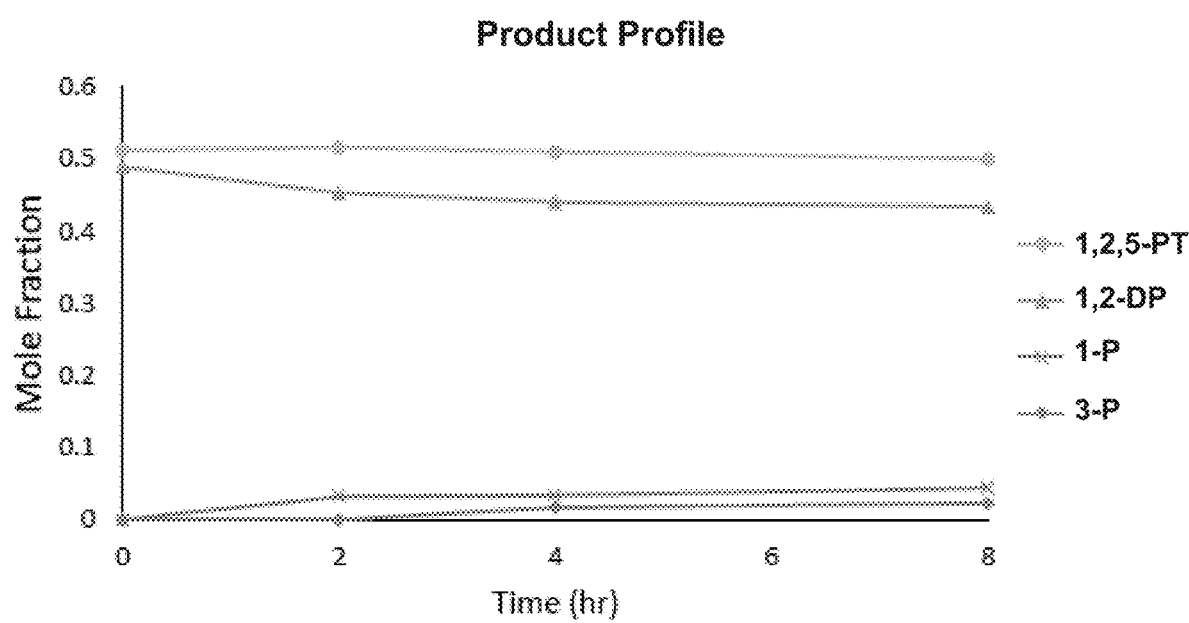
FIG. 1 illustrates a graph showing mole fraction vs. time for the xylitol reaction products.

Repeat use of reference characters in the present specification and drawings is intended to represent the same or analogous features or elements of the present invention.

DETAILED DESCRIPTION

Reference now will be made to embodiments of the disclosure, one or more examples of which are set forth below. Each example is provided by way of an explanation, not as a limitation. In fact, it will be apparent to those skilled in the art that various modifications and variations can be made without departing from the scope or spirit of the disclosure. For instance, features illustrated or described as one embodiment can be used on another embodiment to yield still a further embodiment. Thus, it is intended that the present disclosure cover such modifications and variations as come within the scope of the appended claims and their equivalents. It is to be understood by one of ordinary skill in the art that the present discussion is a description of exemplary embodiments only and is not intended as limiting the broader aspects of the present disclosure, which broader aspects are embodied exemplary constructions.

Generally, the present disclosure is directed to compositions, methods, and processes to produce compounds having the structure:

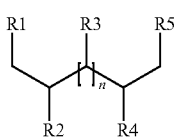

Structure (I)

each of R1-R5 is selected from a hydroxyl group and hydrogen; R1-R5 include at least one hydroxyl group and at least one hydrogen; n=0-2. In particular, methods of the disclosure can include reacting a precursor, the precursor containing more oxygen (O) atoms than the compound, with a gas containing hydrogen ($H_2$) in the presence of a catalyst.

As a non-limiting example, the compound can include 1,2-Dideoxypentitol, which has R1-R3=hydroxyl groups (—OH), R4-R5=hydrogen (—H), and n=1. Reference to 1,2-dideoxypentitol includes stereoisomers having the general structure below:

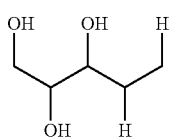

Structure (II)

Another non-limiting example of the compound can include 1,2,5-pentanetriol, which has R1-R2 and R5=hydroxyl groups, R3-R4=hydrogen, and n=1. Reference to 1,2,5-pentanetriol includes stereoisomers having the general structure below:

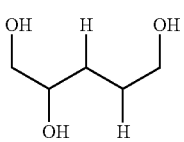

Structure (III)

Generally, the compound is produced from a precursor that can be a carbohydrate or a carbohydrate derivative. In an example embodiment, the carbohydrate or carbohydrate derivate can be an aldose, a ketose, a sugar alcohol, or a sugar acid. In certain embodiments, the precursor can be expressed as having the structure:

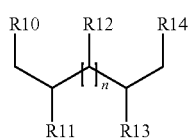

Structure (IV)

each of R10-R14 is selected from a hydroxyl group, a carbonyl group, and a hydrogen; and n=0-2. Though shown as a linear structure, carbohydrates are known to form cyclic hemiacetals such as the six-membered ring pyranoses and five-membered ring furanoses. These and cyclic carbohydrate derivatives can also be used as precursors in certain embodiments of the disclosure. For these embodiments, the cyclic precursor can be expressed as having the structure:

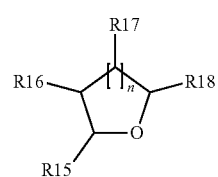

Structure (V)

each of R15-R18 is selected from a hydroxyl group, a hydrogen or a C1-C3 alkoxy group, and n=1-2.

As a non-limiting example, the precursor can include xylitol, which has the structure:

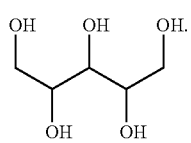

Structure (VI)

In embodiments of the disclosure, a precursor (e.g., a precursor having any of the structures shown above) can be reacted with a gas containing molecular hydrogen ($H_2$) to generate the product compound. For these embodiments, the precursor may be added to a reactor along with a catalyst and the hydrogen containing gas, and the reaction can be conducted at a temperature, pressure, and catalyst concentration. In certain embodiments, the reaction may also include a solvent. After conducting the reaction for a time, the reaction products may be isolated using a purification process such as chromatography, extraction, distillation, or combinations of these.

As an example embodiment, the precursor and the gas containing $H_2$ (e.g., at least 99.9% pure $H_2$) can be added to a reactor designed for batch reaction. Herein, batch reaction is used to indicate that all reaction materials are added to the reactor before a reaction start time (e.g., before the reaction has reached reaction temperature or reaction pressure, or prior to catalyst addition) and no products or substantially no products are removed before a reaction end time. For instance, an example process can include adding the precursor and the catalyst to the reactor, pressurizing the reactor with $H_2$ gas, and heating the reactor to the reaction temperature. The batch reaction is then conducted for a reaction time (e.g., 2 hours, 3 hours, 4 hours, 5 hours, 6 hours, 7 hours, or 8 hours), after which the reactor is cooled, depressurized, or both.

As another example embodiment, the precursor, the gas containing $H_2$ (e.g., 99.9% pure $H_2$), or both reactants can be added to a reactor designed for plug flow, such as a fixed bed reactor, a fluidized bed reactor, a trickle bed reactor, or other reactors configured to allow one or more of the reactants to flow through the reactor while the catalyst is primarily contained in the reaction zone. Herein, plug flow is used to indicate that the reactor includes a reactor bed coupled to an inlet and an outlet. The inlet allows some or all the reactants (e.g., precursor and gas containing $H_2$) to enter the reactor bed continuously at a controlled rate while a product stream exits through the outlet. For these reactors, reaction time can be calculated based on the linear velocity of the reactant stream and the total reactor volume to approximate the residence time of the reactants in the reactor bed. For instance, an example process can include adding the catalyst to the reactor bed, adding the precursor as a solution to the bed, pressurizing the reactor bed with $H_2$ gas, heating the reactor to the reaction temperature, then flowing $H_2$ gas, a precursor solution, or both through the reactor bed.

The reactor designs described herein are meant to be illustrative and are provided as examples that can be practiced with embodiments of the disclosure. Other reactor configurations could be developed and practiced without deviating from the spirit of the invention.

For embodiments of the disclosure, the compounds having Structure (I) can be produced by a process that includes a catalyst. Generally, the catalyst is formed from a support impregnated with a transition metal. Various supports can be used including metal oxides such as ceria ($CeO_2$); zirconia ($ZrO_2$); alumina ($Al_2O_3$); silica ($SiO_2$); titania $TiO_2$; magnesium oxide MgO; calcium oxide CaO; lanthanum oxide $La_2O_3$; yttria $Y_2O_3$; and combinations such as aluminum silicates ($Al_{2x}Si_yO_{3x+2y}$). Additionally, or alternatively, the support can include carbon nitrides, activated carbon, graphene, and/or carbon black. Thus, the materials used to produce the catalyst are not constrained solely to the examples provided below in Table 1.

Catalysts disclosed herein can include any of the above supports impregnated with one or a combination of transition metals. Embodiments of the disclosure can include reacting a precursor with a catalyst impregnated with at least one of the following metals: Re, Os, Ir, Pt, Au, Rh, Pd, and Cu. Exemplary combinations include Re/Pt, Re/Au, ReOs, Re/Rh, Re/Pd, Re/Cu, Au/Pt, and Re/Ir. In embodiments of the disclosure that include a catalyst impregnated with more than one transition metal, the concentrations of each metal may be different or the same.

The catalysts employed in embodiments of the disclosure can be manufactured using a variety of methods. As an example, a catalyst included in an embodiment of the disclosure can be manufactured by wet impregnation using an aqueous solution of ammonium perrhenate and an aqueous solution of palladium (II) nitrate. Other wet or dry impregnation methods can be used to incorporate transition metals into the support so that the total weight percentage of transition metal contained in the support framework is 1-8 wt %.

In Table 1, example ranges for different catalyst compositions are shown for embodiments of the catalyst that includes two transition metals (referenced as TM1 and TM2). The metal or metals are included in the support as a percentage of the total weight of the catalyst. For example, in an embodiment, a reaction can be conducted using a cerium oxide ($CeO_2$) support impregnated with 0-6 wt % Rhenium (Re) and 0-4 wt % Palladium (Pd). In another embodiment, a reaction can be conducted using a zirconium oxide ($ZrO_2$) support impregnated with 0.5-5 wt % Re and 1-2.5 wt % Pd.

TABLE 1

Example Ranges and Catalyst Compositions
Example Catalyst Compositions

| Support | TM1 wt. % | TM2 wt. % |
|---|---|---|
| $CeO_2$ | 0.1-6 | 0-4 |
| $Al_{2x}Si_yO_{3x+2y}$ | 0.5-5 | 0.5-3 |
| $ZrO_2$ | 1-4.5 | 1-2.5 |

As described above, embodiments of the disclosure include reacting a precursor with a gas containing hydrogen in the presence of a catalyst. In one embodiment, the gas containing hydrogen can also include an inert gas. Exemplary inert gases include the noble gases: He, Ne, Ar, Kr, Xe, and Rn. In certain embodiments, nitrogen ($N_2$) can also be used as an inert gas. In some embodiments, the gas containing, hydrogen, may contain substantially only hydrogen, such as 99.9% or greater purity. In other embodiments, the gas containing hydrogen may contain one or more inert gases to modify the volume percentage hydrogen to about 30 vol % to about 98 vol %. Herein, vol % should be calculated based on the volume of gas used, not the total volume.

Embodiments of the disclosure can be practiced over a range of reaction conditions. Exemplary reaction conditions are provided in Table 2.

TABLE 2

Ranges of Reaction Conditions
Example Reaction Conditions

| Temperature ° C. | Pressure (bar) | Catalyst wt % |
|---|---|---|
| 100-240 | 2-40 | 1-25 |
| 120-200 | 4-25 | 2-20 |
| 150-190 | 5-15 | 4-12 |

This disclosure demonstrates an advantage by providing embodiments that can be practiced at low pressures such as pressures below about 40 bar. In certain embodiments, the methods for producing a compound can be conducted at a pressure between about 4 bar to about 25 bar. Additionally, some example embodiments can be conducted at a pressure between about 5 bar to about 15 bar.

In embodiments of the disclosure, the method for producing a compound can also include a reaction temperature. For these embodiments the reaction temperature is generally between about 100° C. to about 240° C. In certain embodiments, the reaction temperature can be between about 120° C. to about 200° C. In some of these embodiments, the reaction temperature can be between about 150° C. to about 190° C. The reaction temperatures provided can be practiced with other reaction conditions, such as pressure and catalyst weight percentage, without limitation, and so should not be held as only used only with the conditions shown in one row of Table 2.

Embodiments of the disclosure can also include a catalyst wt %. The catalyst wt % refers to the percentage of catalyst relative to the weight of the precursor and catalyst. For example, if 2.0 g precursor is reacted with 0.6 g catalyst, the combined weight is 2.6 g, and the wt % catalyst is about 23 wt %.

Some embodiments of the disclosure can include conducting the reaction in a solvent. Suitable solvents can include, but are not limited to, methanol; acetone; dioxane; tetrahydrofuran; dichloromethane; chloroform; carbon tetrachloride; N,N-dimethylformamide; toluene; benzene; benzene derivatives; or mixtures thereof.

In some embodiments, the precursor can be derived from biomass, such as a material containing lignocellulose or a material that includes one or more of cellulose, hemicellulose, or lignin. Processes for deriving carbohydrates or carbohydrate materials from biomass are described in U.S. Pat. Nos. 7,109,005 and 5,424,417, and CN Patent 103 131 802, the disclosures of each of which are incorporated herein by reference in their entirety. Xylose, a carbohydrate that can be used in example embodiments of the disclosure can be derived from xylan, a pentose polymer found widely in plants. Lignocellulosic materials containing xylan can include one or more of the following: wood; softwood as pine; spruce; hardwood as alder aspen, birch, beech, eucalyptus, maple, poplar, willow; plants as plant constituents; grain as wheat, barley, rice, rye and oat; and particulates of grain as straw, hulls, husks, fiber, shells, stems, corn cobs, corn straw, corn fiber, nutshells, almond shells, coconut shells, bagasse, cotton seed bran, cotton seed skins; wood chips, sawdust, wood pulp, processed paper, spent sulphite liquor, spent liquor from paper processing, spent liquor from wood pulp processing, sulphite cooking liquor; or liquids derived from any of the preceding. These materials are provided by way of example and are not meant to limit the scope of lignocellulosic materials from which the precursor can be derived.

Processes for deriving xylan or monosaccharides from lignocellulose may include a pretreatment which can include mechanical processing, acidic conditions, elevated temperatures, and/or pressure swings. An exemplary pretreatment may include steam explosion. After pretreatment, polysaccharides and oligosaccharides, such as xylan, may require hydrolysis under acidic conditions or using an enzyme to produce the carbohydrate monomers and carbohydrate derivates used in embodiments of the disclosure. Example hydrolysis processes and conditions are described further in U.S. Pat. Nos. 3,586,537 and 3,784,408, the disclosure of each of which is incorporated herein by reference in its entirety. As an example, a solution containing xylan can be combined with oxalic acid to produce xylose. It has been found that oxalic acid can hydrolyze xylan, while not hydrolyzing cellulose, providing a method that can isolate soluble pentoses, while leaving the hexoses as insoluble polymers.

There exist a wide variety of processes for deriving sugar alcohols from carbohydrates such as xylose. The general reaction is a reduction of the carboxyl group on the carbohydrate to a hydroxyl group, and so any method for selectively reducing carbonyl groups can be practiced to derive the sugar alcohol. In certain embodiments of this disclosure, the sugar alcohol can be derived from carbohydrates obtained from biomass. As noted, processes for generating a variety of precursors have been described in the literature, though improvements are continuing to be made. This disclosure generally provides methods and processes for deriving value compounds from the carbohydrates and carbohydrate derivatives, which in certain embodiments can be obtained from lignocellulosic biomass.

EXAMPLE 1

Example 1 discusses a study using various methods and procedures. The study supports exemplary embodiments that may be understood in conjunction with the Drawings and Description provided herein.

Generally, reactions were conducted in a stainless steel high-pressure batch reactor at a pressure, temperature, and catalyst weight loading. For instance, a reaction as disclosed herein can be conducted at a temperature between 100-240° C., a pressure between 2-40 bar, and a catalyst loading between 1-25 wt %.

In an example reaction, 2 g xylitol was added into a batch reactor along with 0.60 g of 4 wt % catalyst. Dioxane was added to the reactor along with a stir bar, and the reactor sealed and checked for leaks using an inert gas. The reactor was brought to a reaction temperature of 160° C. and charged with a gas containing substantially pure $H_2$ to a pressure of 10 bar. The reaction was conducted over a period of 4 hours, and the concentration of 1,2-dideoxypentitol; 1,2,5-pentanetriol; 1-pentanol; and 3-pentanol was monitored over the course of reaction. After 4 hours, the conversion of xylitol was calculated as 59.4%.

In another example reaction, 2 g xylitol was added into the high-pressure reactor along with 0.60 g of a 4 wt % catalyst. Dioxane was added to the reactor along with a stir bar, and the reactor sealed and checked for leaks using an inert gas. The reactor was brought to a reaction temperature of 160° C. and the reactor was charged with a gas containing substantially pure $H_2$ to a pressure of 5 bar. The reaction was conducted over a period of 4 hours, and the concentration of 1,2-dideoxypentitol; 1,2,5-pentanetril; 1-pentanol; and 3-pentanol was monitored over the course of reaction. After 4 hours, the conversion of xylitol was calculated as less than 5%.

In an additional example reaction, 2 g xylitol was added into the high-pressure reactor along with 0.60 of a 4 wt % catalyst. Dioxane was added to the reactor along with a stir bar, and the reactor sealed and checked for leaks using an inert gas. The reactor was charged with a gas containing substantially pure $H_2$ to a pressure of about 27.5 bar. The reactor was then brought to a reaction temperature of 160° C. increasing the reactor pressure to about 40 bar. The reaction was conducted over a period of 16 hours, and the concentration of 1,2-dideoxypentitol; 1,2,5-pentanetriol; 1-pentanol; and 3-pentanol was monitored over the course of reaction. The reaction demonstrated varying conversion over the reaction time including higher conversions from about 1.5 hours to about 8.5 hours for producing value compounds 1,2-dideoxypentitol and 1,2,5-pentanetriol.

The catalysts used in the disclosed examples were made by wet impregnation using an aqueous solution of ammonium perrhenate and an aqueous solution of palladium (II) nitrate. Catalysts used in embodiments of the disclosure can be formed from using alternative methods, and may contain Re, Pd, or mixtures thereof. Thus, methods of the disclosure are not, and should not be, limited to the conditions or materials provided in the disclosed examples. These examples are provided for illustrative purposes only.

FIGS. 1A and 1B illustrate an exemplary embodiment of the disclosure. In FIG. 1A, a graph is illustrated showing the mole fraction of four different products as a function of time. The reaction was conducted at 40 bar and 160° C. using xylitol as the precursor. The four products 1,2,5-PT; 1,2-DP; 1-P; and 3-P refer to 1,2,3-pentanetriol; 1,2-dideoxypentitol; 1-pentanol; and 3-pentanol respectively. FIG. 1B illustrates the same graph in grayscale.

Figure 2:
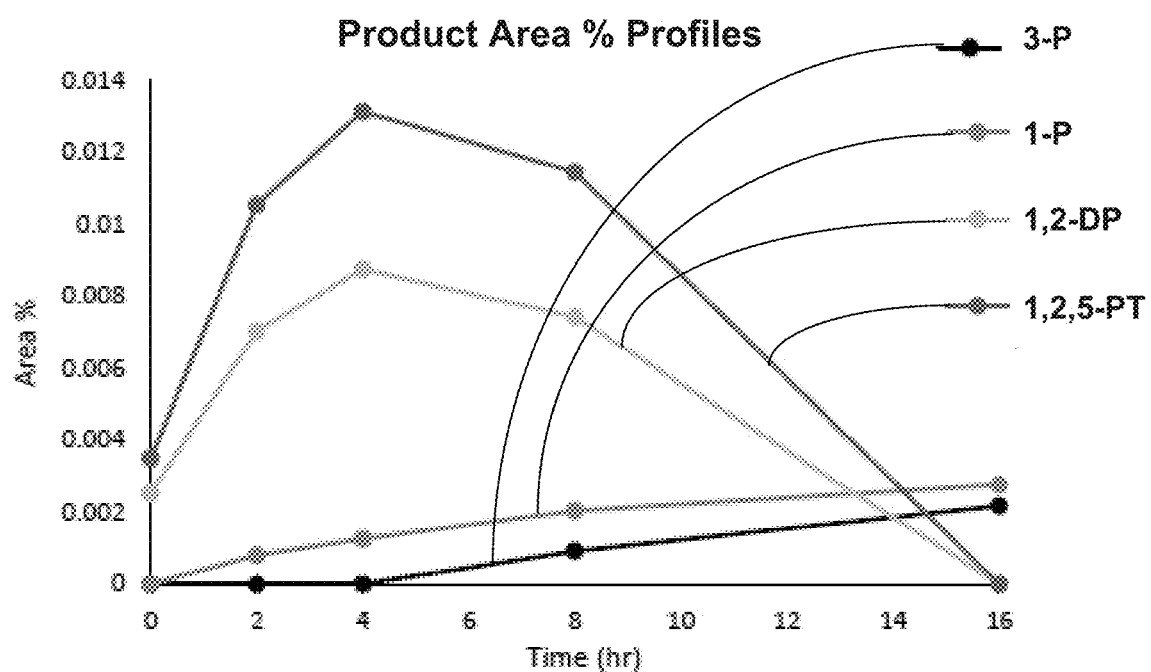
FIG. 2 illustrates a graph showing Area % vs. time for the product area profiles of the reaction products.

FIGS. 2A and 2B further illustrate an exemplary embodiment of the disclosure. In FIG. 2A, a graph is illustrated showing the Area % of 1,2,5-PT; 1,2-DP; 1-P; and 3-P as a function of time. The four products and the reaction conditions are the same as shown in FIGS. 1A and 1B. FIG. 2B illustrates the same graph in grayscale. Note that as used herein, Area % refers to the area under the curve of each reaction compound detected using gas chromatography (GC) relative to the total area. Though not shown, dioxane is detected as a reaction compound, thus the total Area % of the reaction products does not sum to 1.

Figure 3:
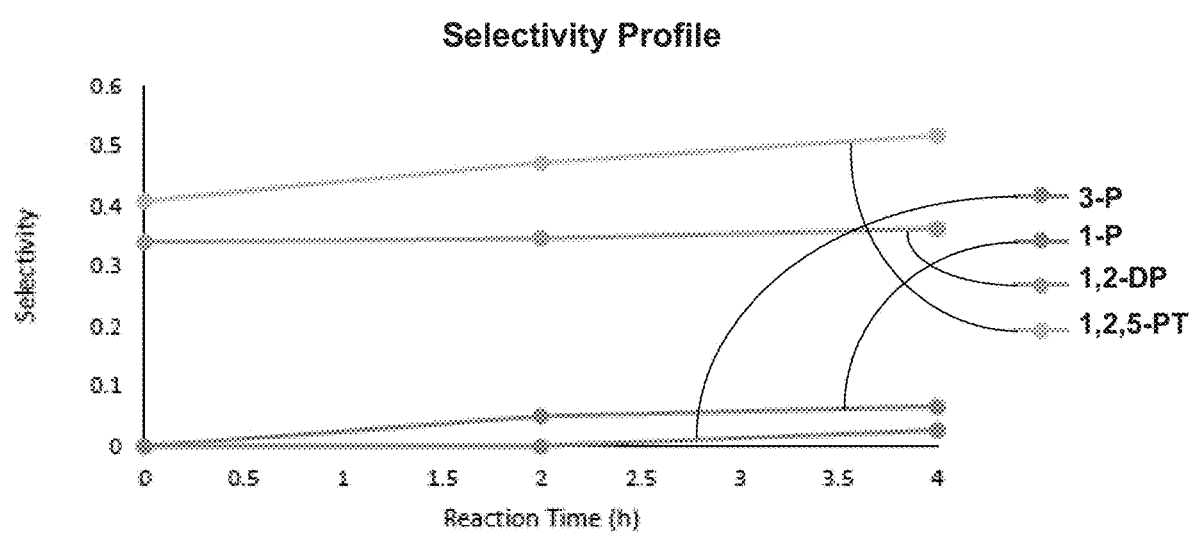
FIG. 3 illustrates graph showing selectivity vs. reaction time for the reaction products.

FIGS. 3A and 3B illustrate an exemplary embodiment of the disclosure. In FIG. 3A, a graph is illustrated showing selectivity of 1,2,5-PT; 1,2-DP; 1-P; and 3-P as a function of time. The reaction was conducted at 10 bar and 160° C. using xylitol as the precursor. FIG. 3B illustrates the same graph in grayscale. Note that as used herein, selectivity refers to the GC peak area of each compound, relative to the total area of the reaction products.

Figure 4:
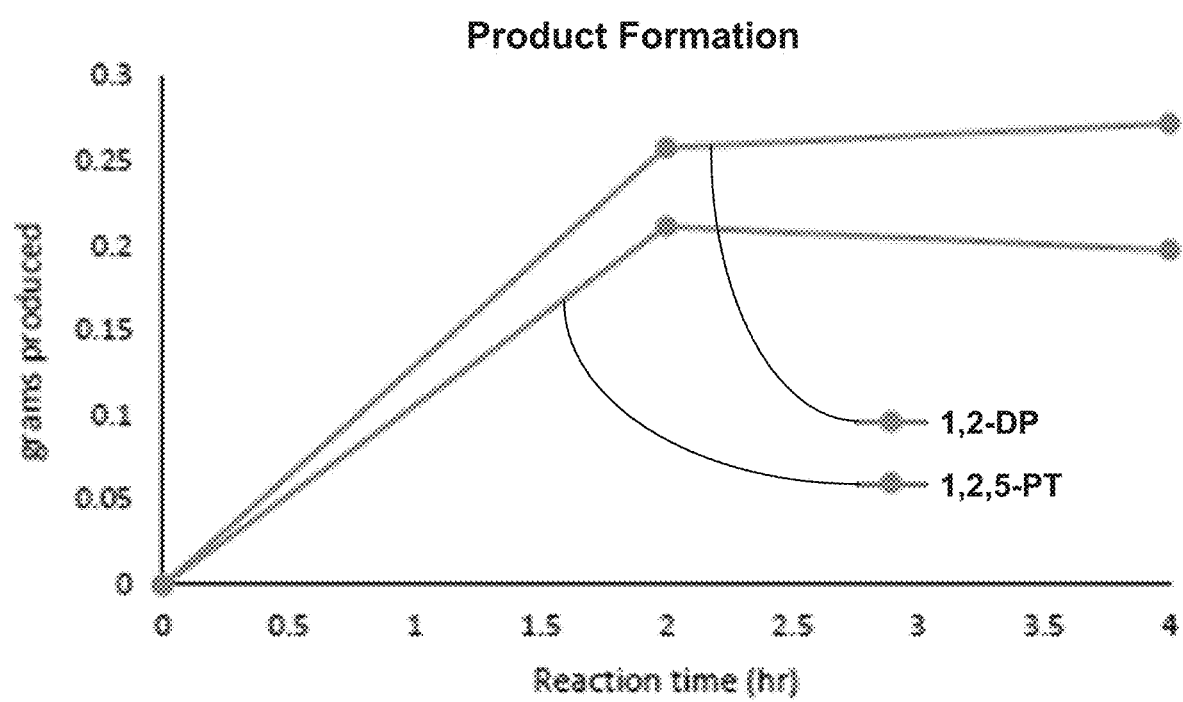
FIG. 4 illustrates a graph showing grams produced vs. reaction time for the reaction products.

FIGS. 4A and 4B illustrate an exemplary embodiment of the disclosure. In FIG. 4A, a graph is illustrated showing grams of product for 1,2-DP and 1,2,5-PT produced as a function of time. The reaction is conducted at 5 bar and 160 C using xylitol as the precursor. FIG. 4B illustrates the same graph in grayscale.

Figure 5A:
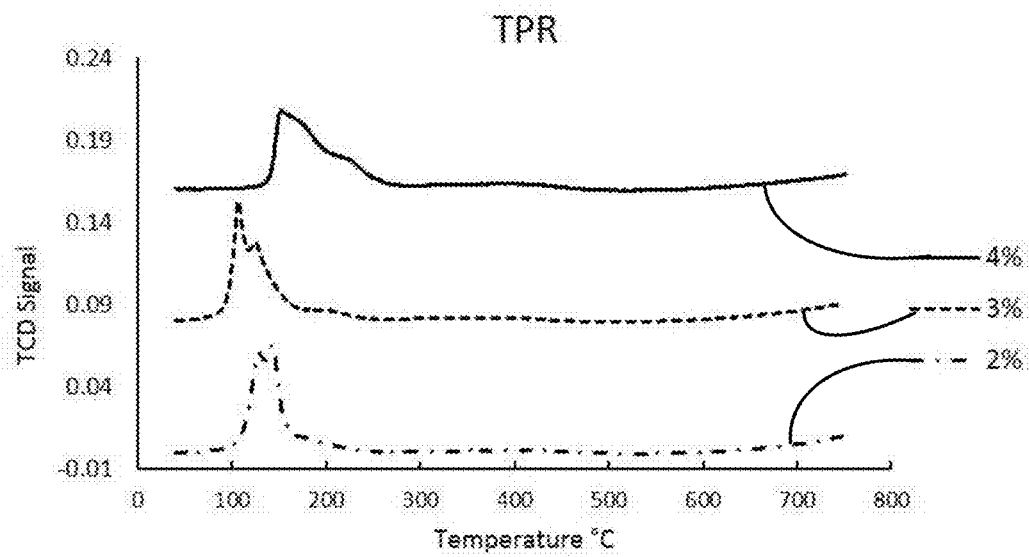
FIG. 5A illustrates a graph showing temperature-programmed reduction (TRP) curves for 3 different catalyst loadings: 4%, 3%, and 2%.

FIG. 5A illustrates a graph providing a TPR analysis of three different embodiments of the catalyst. The top curve shows a TCD signal for a ceria support impregnated with 4 wt % (4%) Re. The middle curve shows a TCD signal for a ceria support impregnated with 3 wt % Re and the bottom curve shows a TCD signal for a ceria support impregnated with 2 wt % Re.

Figure 5B:
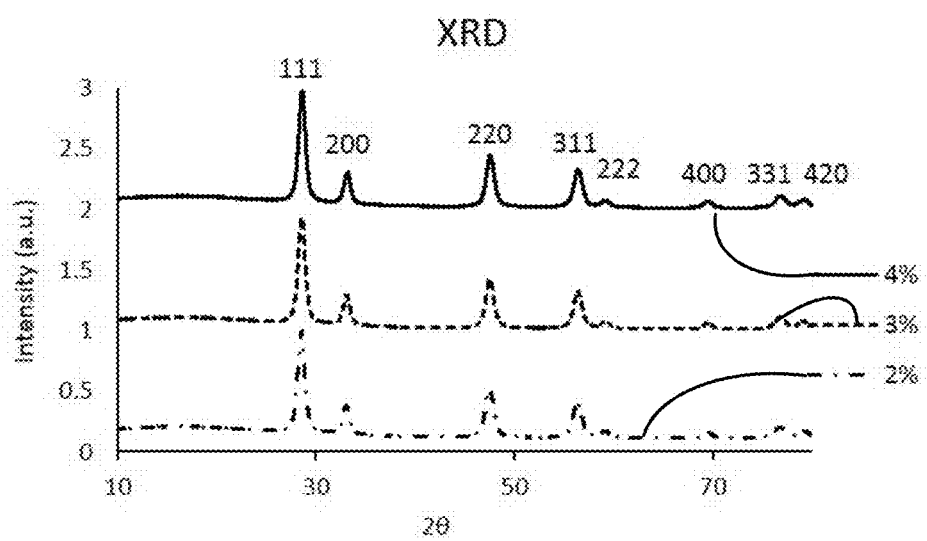
FIG. 5B illustrates a graph showing X-ray diffraction (XRD) curves for 3 different catalyst loadings: 4%, 3%, and 2%.

FIG. 5B illustrates a graph providing an XRD analysis of three different embodiments of the catalyst. The top curve shows an intensity signal for a ceria support impregnated with 4 wt % (4%) Re. The middle curve shows an intensity signal for a ceria support impregnated with 3 wt % Re and the bottom curve shows an intensity signal for a ceria support impregnated with 2 wt % Re.

An inductively coupled plasma (ICP) analysis for each of the catalyst embodiments is provided in Table 3.

TABLE 3

ICP analysis of catalyst embodiments

| Nominal Re Loading (wt %) | Measured Loading (wt %) | Error (wt %) |
|---|---|---|
| 2 | 1.528 | 0.106 |
| 3 | 2.508 | 0.168 |
| 4 | 3.304 | 0.144 |

Figure 6:
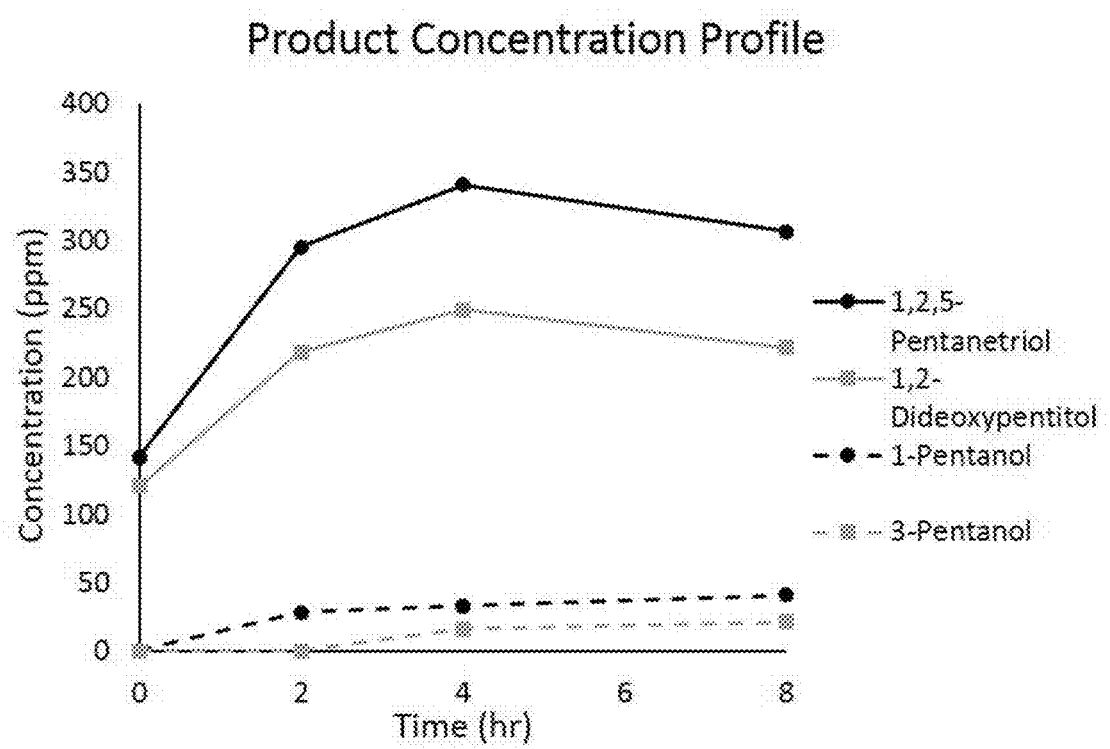
FIG. 6 illustrates a graph displaying the concentration profile for 4 compounds versus time.

FIG. 6 illustrates an exemplary embodiment of the disclosure showing product concentration versus time for an example reaction. The reaction is conducted at 40 bar and 160° C. using xylitol as the precursor.

Figure 7A:
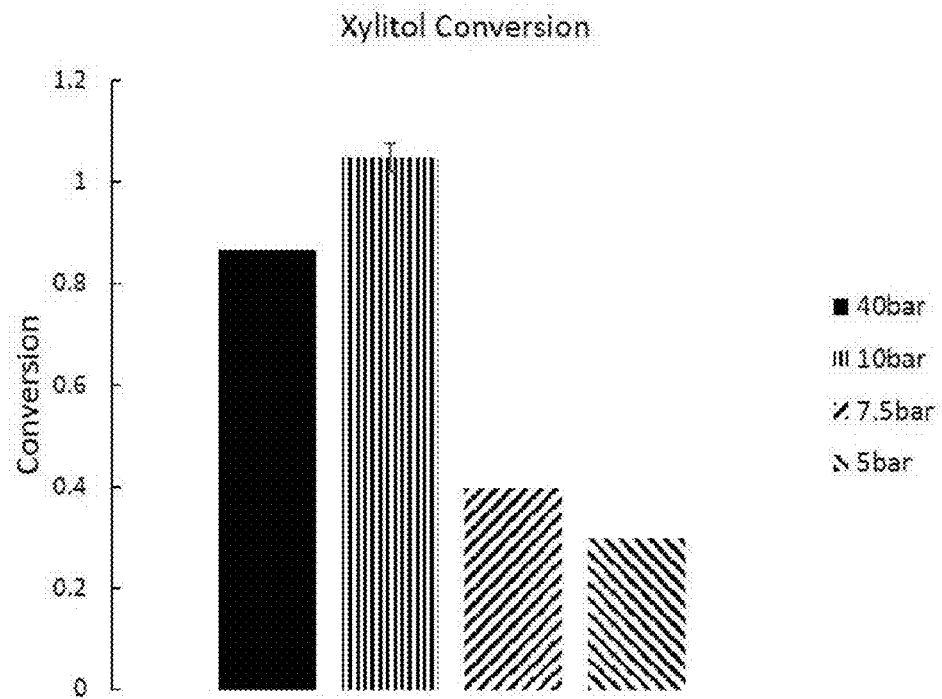
FIGS. 7A-7B illustrate graphs displaying conversion and selectivity, respectively, at 4 different pressures: 40 bar, 10 bar, 7.5 bar, and 5 bar.
Figure 7B:
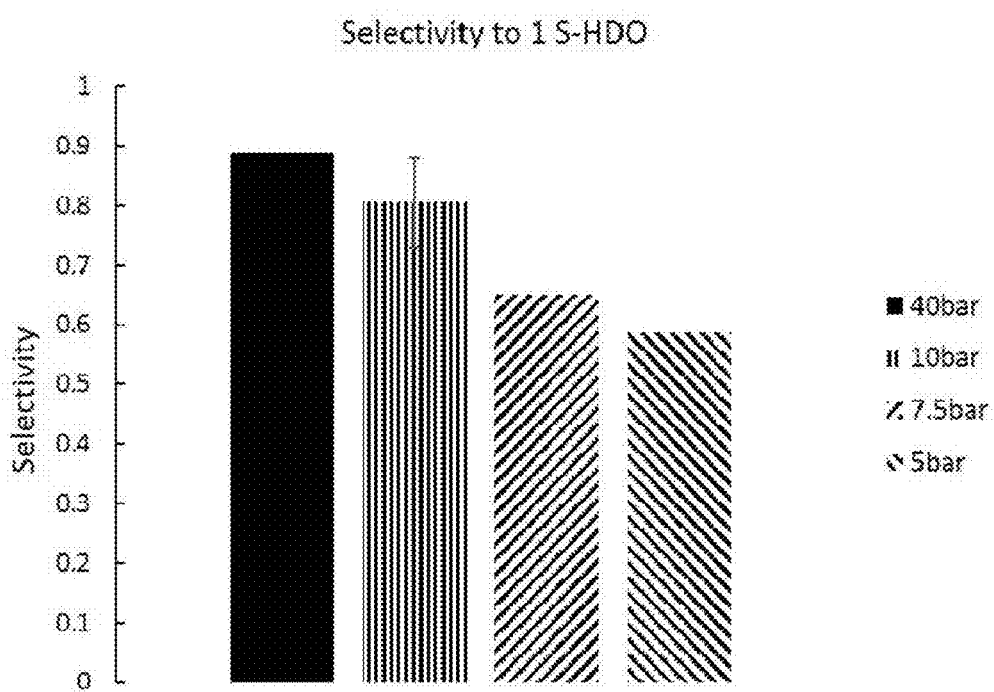

FIGS. 7A and 7B illustrate an exemplary embodiment of the disclosure showing xylitol conversion and selectivity to 1 S-HDO, respectively, at different pressures. As defined herein, 1 S-HDO refers to the combination of 1,2-dideoxypentitol and 1,2,5-pentanetriol. The graphs provide data after 4 hr for reactions conducted at various pressures ranging from 5 bar to 40 bar at 160° C. using xylitol as the precursor.

Figure 8A:
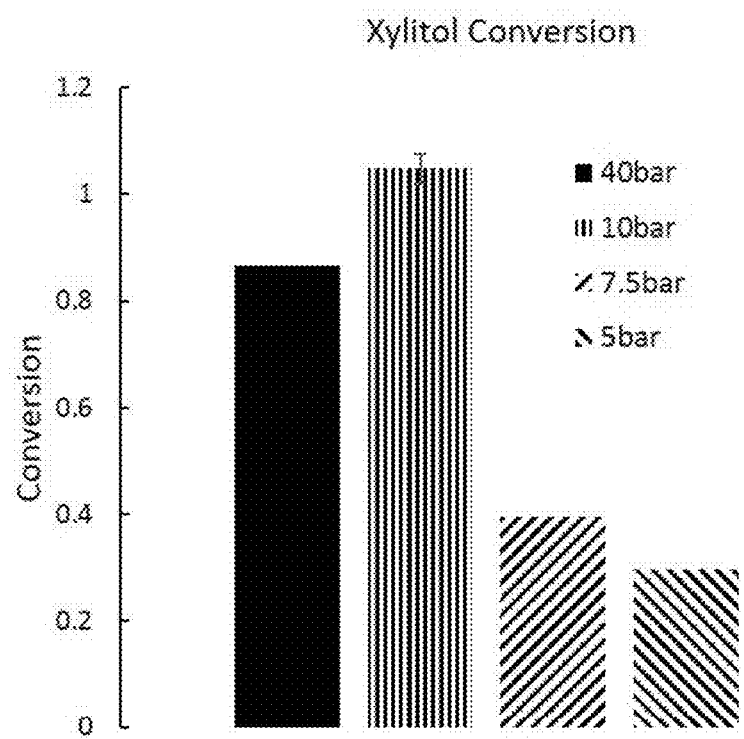
FIGS. 8A-8B illustrate graphs displaying conversion and yield, respectively, at 4 different pressures: 40 bar, 10 bar, 7.5 bar, and 5 bar.
Figure 8B:
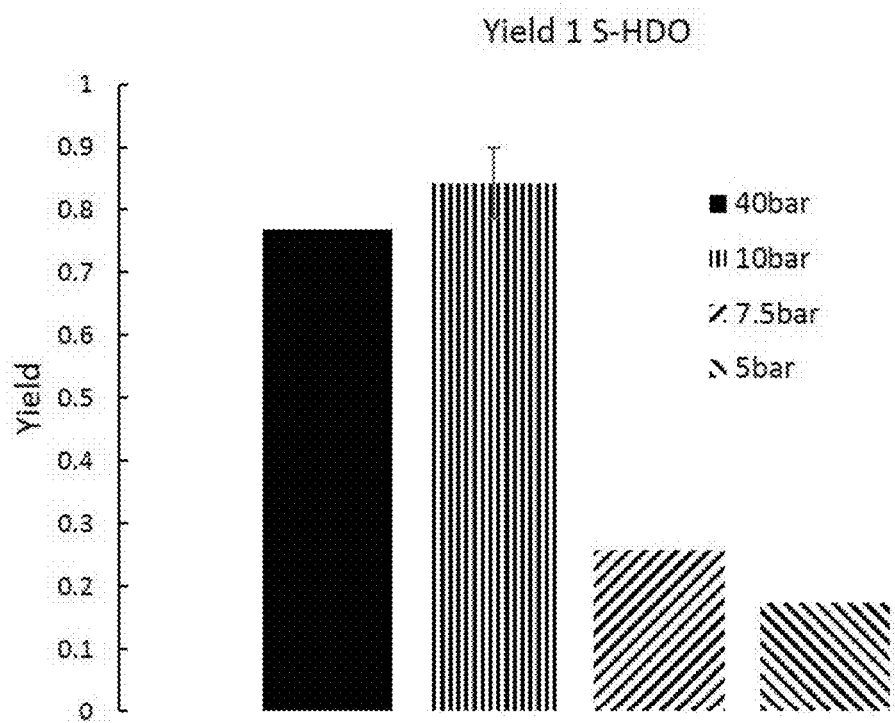

FIGS. 8A and 8B illustrate an exemplary embodiment of the disclosure showing xylitol conversion and yield 1 S-HDO, respectively, at different pressures. The graphs provide data after 4 hr for reactions conducted at various pressures ranging from 5 bar to 40 bar at 160° C. using xylitol as the precursor.

The invention claimed is:

1. A method for the production of a compound, the method comprising: reacting a precursor, the precursor comprising a carbohydrate or a carbohydrate derivative containing a greater number of oxygen atoms than the compound, with a gas containing $H_2$ in the presence of a catalyst, at a pressure less than about 40 bar; the compound comprising:

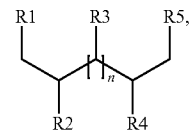

wherein each of R1-R5 is selected from the group consisting of: a hydroxyl group and hydrogen; and wherein R1-R5 comprise at least one hydroxyl group and at least one hydrogen; and wherein n=0-2, and wherein the catalyst comprises a support comprising $CeO_2$ and the support is impregnated with both Re and Pd.

2. The method of claim 1, wherein the compound is selected from one at least one of:

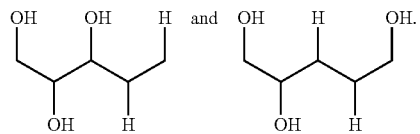 [SMILES: CCC(O)C(O)CO ; "and" ; OCCCC(O)CO]

3. The method of claim 1, wherein the carbohydrate or carbohydrate derivative is selected from the group consisting of: an aldose, a ketose, a sugar alcohol, and a sugar acid.

4. The method of claim 1, the precursor comprising:

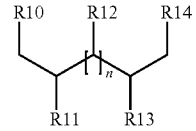

wherein, each of R10-R14 is selected from the group consisting of: a hydroxyl group, a carbonyl group, and a hydrogen; and wherein, n=0-2.

5. The method of claim 4, wherein each of R10-R14 is selected from the group consisting of: a hydroxyl group, and a hydrogen.

6. The method of claim 4, wherein each of R10-R14 is a hydroxyl group.

7. The method of claim 1, wherein reacting the precursor with a gas occurs at a reaction temperature between about 100° C. to about 240° C.

8. The method of claim 7, wherein the reaction temperature is between about 120° C. to about 200° C.

9. The method of claim 7, wherein the reaction temperature is between about 130° C. to about 180° C.

10. The method of claim 7, wherein the reaction pressure is between about 4 bar and about 25 bar.

11. The method of claim 1, wherein reacting the precursor with a gas occurs at a catalyst loading between about 1 wt % to about 25 wt %.

12. The method of claim 11, wherein the catalyst loading is between about 2 wt % and about 6 wt %.

13. The method of claim 1, wherein the catalyst is impregnated with less than 10 wt % Re and less than 10 wt % Pd.

14. The method of claim 1, wherein the catalyst is impregnated with less than 5 wt % Re and less than 3 wt % Pd.

15. The method of claim 1, wherein the gas containing $H_2$ is greater than 90 vol % $H_2$.

16. A process for converting a carbohydrate or carbohydrate derivative to a compound, the process comprising:
   adding the carbohydrate or carbohydrate derivative to a reactor containing a catalyst;
   reacting the carbohydrate or carbohydrate derivative with a gas containing hydrogen at a reaction pressure and a reaction temperature over a reaction time; and
   purifying a portion of the compound from a product stream,
   wherein, the reaction pressure is less than 40 bar, the reaction temperature is between about 120° C. to about 200° C., and the reactor is designed for batch reaction, and
   wherein the catalyst comprises a support comprising $CeO_2$ and the support is impregnated with both Re and Pd.

17. The method of claim 16, wherein the reaction pressure is less than 15 bar and the reaction time is less than 10 hours.

18. The method of claim 16, wherein the precursor is derived from a lignocellulose containing material.

\* \* \* \* \*